(12) United States Patent
Siniaguine

(10) Patent No.: US 7,448,186 B2
(45) Date of Patent: Nov. 11, 2008

(54) WOUND DRESSING AND APPARATUS FOR FORMING SAME

(75) Inventor: Oleg Siniaguine, San Carlos, CA (US)

(73) Assignee: PolyRemedy, Inc., Mountain View, CA (US)

( * ) Notice: Subject to any disclaimer, the term of this patent is extended or adjusted under 35 U.S.C. 154(b) by 492 days.

(21) Appl. No.: 11/183,459

(22) Filed: Jul. 18, 2005

(65) Prior Publication Data

US 2006/0020235 A1      Jan. 26, 2006

Related U.S. Application Data

(60) Provisional application No. 60/588,628, filed on Jul. 16, 2004.

(51) Int. Cl.
*B65B 63/00* (2006.01)
(52) U.S. Cl. ............... 53/513; 53/431; 53/435
(58) Field of Classification Search .......... 53/431, 53/435, 450, 463, 477, 513, 545; 602/43, 602/48, 54
See application file for complete search history.

(56) References Cited

U.S. PATENT DOCUMENTS

| | | | | |
|---|---|---|---|---|
| 3,140,572 | A | * | 7/1964 | Petersen et al. ............... 53/435 |
| 3,729,892 | A | * | 5/1973 | Aslund et al. ................ 53/435 |
| 4,522,203 | A | | 6/1985 | Mays |
| 4,630,426 | A | * | 12/1986 | Gentry ........................ 53/435 |
| 5,489,437 | A | * | 2/1996 | Marra ........................ 424/443 |
| 5,681,579 | A | | 10/1997 | Freeman |
| 5,762,620 | A | * | 6/1998 | Cartmell et al. ............... 602/48 |
| 5,899,871 | A | * | 5/1999 | Cartmell et al. ............... 602/48 |
| 6,062,285 | A | * | 5/2000 | Dotta et al. ................... 53/435 |
| 6,655,112 | B1 | * | 12/2003 | Cremer et al. ................ 53/435 |
| 6,753,454 | B1 | | 6/2004 | Mello et al. |
| 6,765,123 | B2 | * | 7/2004 | de Jong et al. ................ 602/43 |
| 6,967,261 | B1 | * | 11/2005 | Soerens et al. ................ 602/48 |
| 2006/0020235 | A1 | | 1/2006 | Siniaguine |
| 2006/0034816 | A1 | * | 2/2006 | Davis et al. ................. 424/455 |

OTHER PUBLICATIONS

International Search report, PCT/US05/25362, mailing date Sep. 01, 2006.
Written Opinion of the International Searching Authority, PCT/US05/25362.
International Search Report, PCT/US08/50762, mailing date Jun. 25, 2008.
Written Opinion of the International Searching Authority, PCT/US08/50762.

* cited by examiner

*Primary Examiner*—Louis K Huynh
(74) *Attorney, Agent, or Firm*—MacPherson Kwok Chen & Heid LLP

(57) ABSTRACT

A multi-layered wound dressing includes a moisture-retaining portion for enhancing the healing of a wound. The wound dressing includes an intermediate layer that has both water soluble and water insoluble fibers. An apparatus that includes a cutting tool and a reservoir of liquid to pre-moisten a portion of the dressing may be used to manufacture the dressings.

14 Claims, 12 Drawing Sheets

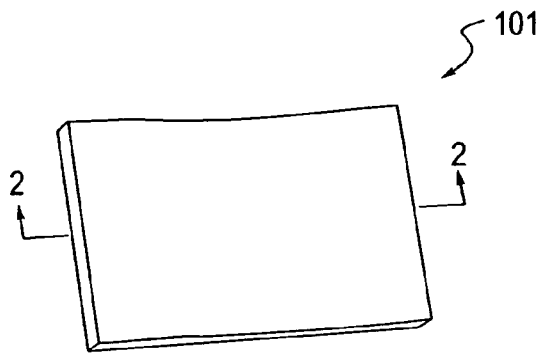
FIG. 1
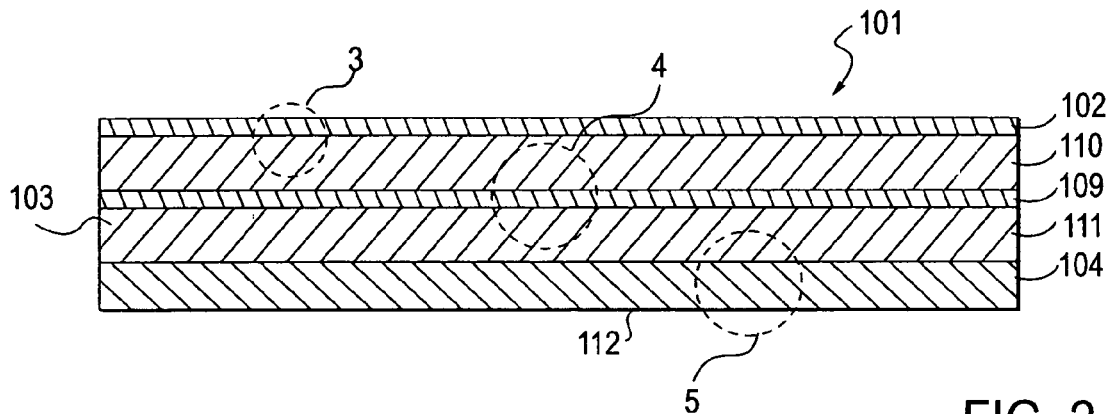
FIG. 2
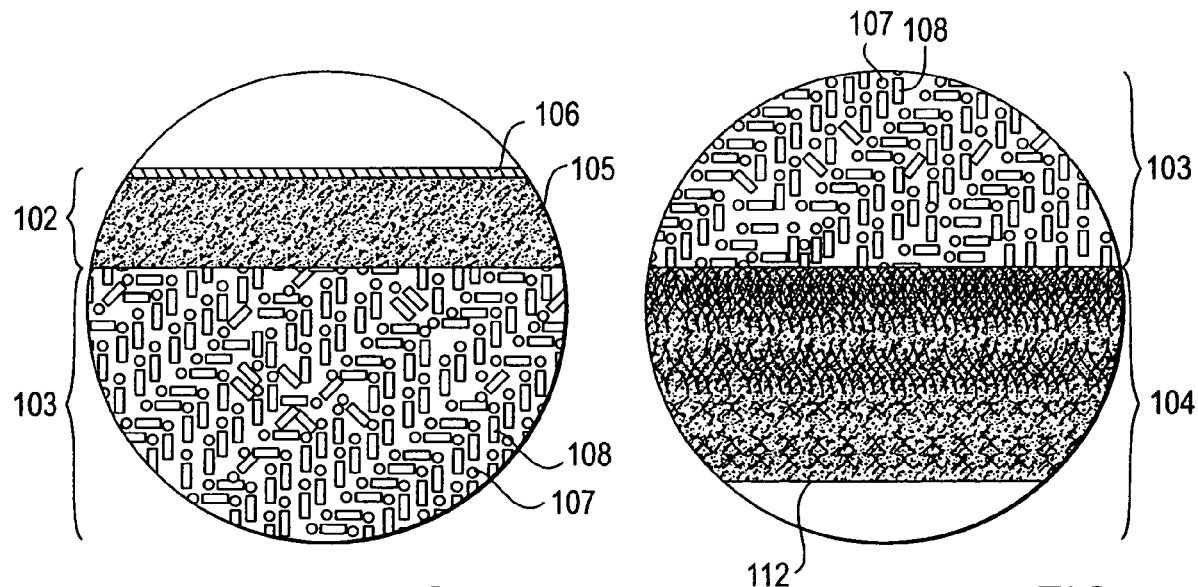
FIG. 3
FIG. 5

WOUND DRESSING AND APPARATUS FOR FORMING SAME

This application claims priority from U.S. Provisional Application No. 60/588,628, filed Jul. 16, 2004, the entire contents of which are hereby incorporated by reference.

FIELD OF INVENTION

The present invention relates to wound dressings and apparatuses for manufacturing the same.

BACKGROUND OF THE INVENTION

Currently, the prevalent method of wound treatment is to cover a wound with a wound dressing. The wound dressing is manufactured as a precut sheet of multi-layer material of various shapes and sizes. The wound dressing is applied to cover the wound and often a portion of the surrounding healthy skin. Sometimes the wound dressing is cut to reduce the size and to better fit the wound size and shape. This reduces the amount of healthy skin covered by the dressing.

A typical wound commonly has two or more different regions or areas, including necrotic, sloughy, bacteria colonized, granulating, epitheliazing, bleeding, exuding, and drying, which are surrounded by healthy skin tissue. The wound and its areas are usually of irregular shapes. Consequently, covering the whole wound area and surrounding healthy skin with the same dressing type may create adverse conditions for certain areas of the wound or the surrounding skin, which may increase the healing time or even cause adverse effects such as secondary dermatitis.

Some of the principals of wound treatment are: (a) to keep wound moist, (b) to control excessive exudates, and (c) to keep healthy skin dry. However, the intensity of exudation can vary as the wound heals. As a result, a dressing, intended for several days of use has to be able to adapt to the changing wound conditions.

Accordingly, there is a need for a method for addressing a wound that provides the optimal targeted moisture control conditions for wound healing by matching the size, shape, and water and water vapor retaining properties of a wound dressing to the targeted wound areas and changing wound conditions. There is a further need for an apparatus to produce such a wound dressing.

BRIEF SUMMARY OF THE DRAWINGS

FIG. 1 is an isometric view of a piece of material suitable for use in forming a wound dressing according to the present invention;

FIG. 2 is a cross sectional view of the piece of material shown in FIG. 1 taken along line 2-2 of FIG. 1;

FIG. 3 is enlarged view of a portion of FIG. 2, illustrating the interface between the outer layer and the intermediate layer of the piece of material of FIG. 1, identified by the circle labeled 3 in FIG. 2;

FIG. 5 is an enlarged view of a portion of FIG. 2 illustrating the interface between the intermediate layer and the inner layer of the piece of material of FIG. 1, identified by the circle labeled 5 in FIG. 2;

SUMMARY OF INVENTION

Figure 4:
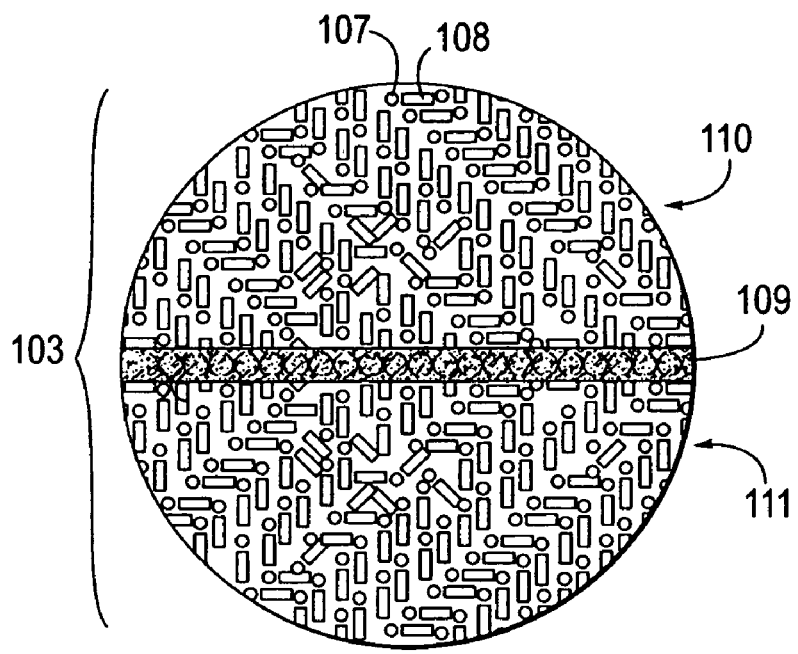
FIG. 4 is an enlarged view of a portion of FIG. 2, illustrating the intermediate layer of the piece of material of FIG. 1, identified by the circle labeled 4 in FIG. 2.

According to one embodiment, the present invention provides a dressing for use on a wound of a mammalian body. The dressing includes a protective outer layer that is substantially impermeable to water. An inner layer adapted for engaging the wound is formed from a material that is at least partially hydrophilic. An intermediate layer is disposed between the inner and outer layers and is formed of a material that is water-soluble and a material that is water-insoluble. Each of the layers may be made from non-woven materials.

According to another embodiment, the present invention relates to a package for treating a wound of a mammalian body. A wound dressing is provided within an airtight internal chamber of a container. The dressing includes a protective outer layer that is substantially impermeable to water. An inner layer adapted for engaging the wound is formed from a material that is at least partially hydrophilic. An intermediate layer is disposed between the inner and outer layers and is formed of a material that is water-soluble and a material that is water-insoluble. Each of the layers may be made from non-woven materials. A layer of adhesive is applied to an exposed surface of the inner layer for attaching the dressing to the skin of the wounded body.

According to another embodiment, the present invention provides an apparatus for use with a strip of material to form a wound dressing. The apparatus includes a frame, a stage provided on the frame, and a dispenser provided on the frame for dispensing a portion of the strip on to the stage. A cutting tool is provided along with a cutting tool mechanism for selectively moving the cutting tool relative to the stage to cut the portion of the strip of material into a wound dressing of a desired shape. A reservoir of moisturizing substance and a moisturizing solution mechanism carried by the frame are provided to apply a moisturizing substance on at least a portion of the wound dressing to moisturize the portion of the wound dressing.

DETAILED DESCRIPTION OF PREFERRED EMBODIMENTS

Shown generally in the drawings is a material that is useful in forming wound dressings. A piece of this material 101 according to one embodiment is shown in FIG. 1. While a rectangular piece of material 101 is shown in FIG. 1, it should be appreciated that the material may be formed or manufactured any desired shape. Most preferably it will be formed in long sheets, or strips, suitable for mounting on rollers or spindles. The piece of material 101 is preferably comprised of non-woven fibers of various types arranged in a layered formation (see FIG. 2). The preferred embodiment for the piece of material 101 includes at least three layers: a protective outer layer 102, an intermediate layer 103, and a wound facing inner layer 104. The purpose of the outer layer 102 is to repel water and serve as a base barrier for bacteria and other contaminants. The intermediate layer 103 serves to absorb and retain liquid in order to keep the wound moist, and also to remove excess exudate. The inner layer 104 provides a surface for contact with the wound and user's skin.

In the preferred embodiment shown, as seen in FIG. 3, the protective outer layer 102 includes an outer micro-fiber layer 105 that is adjacent to the intermediate layer 103, and an exterior grid or film layer 106. Alternatively, the protective outer layer 102 may be formed by either the outer micro-fiber layer 105 without the exterior grid layer 106, or, by the exterior grid layer 106 without an outer micro-fiber layer 105. The thickness of the entire outer layer 102 is preferably within the range of about 10 to 300 microns.

The outer micro-fiber layer 105 preferably has a thickness within the range of about 1 to 100 microns. The outer microfiber layer 105 is preferably made from a material that is a synthetic polymer that is at least partially hydrophobic. Most preferably, the material used to form the outer micro-fiber layer 105 is completely hydrophobic. Preferably the microfibers used to form the outer micro-fiber layer 105 have a diameter ranging from between 0.01 to 100 microns. The micro-fibers within the outer micro-fiber layer 105 are preferably packed together to form a mesh having an average pore size between fibers of less than one micron. Preferably the pore size of the outer micro-fiber layer 105 is such that the layer is impermeable for liquid water, airborne contaminates, and bacteria, but permeable to water vapor, air, and gases. Examples of suitable polymers that may be used to form the micro-fibers in the outer micro-fiber layer 105 include polymers such as poly(caprolactone), poly(L-lactic acid), poly (glycolic acid) and similar co-polymers of these acids, and any other partially hydrophobic material suitable for forming fibers. The micro-fibers may be colored for matching patient skin color, or other reasons. Other additives or adjuvants may be incorporated into the fibers to enhance anti-bacterial or anti-viral properties, or to absorb odors.

Suitable methods can be utilized for forming the microfibers, as well as for depositing the micro-fibers in a layer of suitable thickness and pore size to form the outer micro-fiber layer 105. Such techniques may include electrospinning from a solution, gas blowing from a melt, or any other known technology. A suitable and preferred technique is described in co-pending U.S. patent application Ser. No. 10/431,888 filed May 7, 2003, and U.S. patent application Ser. No. 10/382,422 filed Mar. 5, 2003, the entire content of each of which is hereby incorporated herein by this reference.

The exterior grid layer 106 preferably includes elongated strips that form a Protective outer barrier. The preferred individual strips may have thicknesses ranging from approximately 50 microns to approximately 10 millimeters. The material for forming the strips may be non-porous or porous, hydrophobic or hydrophilic, transparent, opaque or colored. The material may be natural or synthetic fibers or fabric. A hydrophobic polymer preferably forms the strips. The strip thickness is chosen in order to provide mechanical strength and support to the dressing while still permitting a dressing made from the material to be lightweight and flexible. The strips may cross each other with various angles depending on a chosen pattern. The pattern may be perpendicular, angular, radially coaxial, or random. The pattern and distance between neighboring strips may vary within the dressing as desired.

Other methods for forming the strips may include: pressure or jet spray, ultrasonic spray, electro dynamic spray in an electrostatic field, droplet placement, and solution or melt dispensing. Various methods can be utilized for controlling the thickness and width of the strips as they are formed. Suitable and preferred techniques are described in pending U.S. patent application Ser. No. 10/431,888 filed May 7, 2003.

Intermediate layer 103, shown in the enlarged view of FIG. 4, comprises primarily a mixture of water-soluble fibers 107 and water insoluble fibers 108. The water-soluble fibers 107 are shown as circles, whereas the water-insoluble fibers 108 are shown as rectangles. This convention was used for convenience, and does not relate to the appearance of the fibers themselves. The insoluble fibers 108 act as a scaffold, or support structure, for the intermediate layer 103. As will be described in more detail later, the water-soluble fibers 107 dissolve when liquid is added to the intermediate layer 103, either through addition of a moisturizing agent or by excess liquid pulled from the wound. While drying due to evaporation through the outer layer 102, these dissolved soluble fibers form a continuous polymer film that serves as a barrier to the underlying portion of the dressing to preclude or inhibit evaporation.

One or more layers of hydrophilic fibers act as a dividing layer 109 made of a material that is insoluble in water may subdivide the intermediate layer 103. In the embodiment shown in FIGS. 2 and 4, a single dividing layer 109 is used to divide the intermediate layer 103 into a first intermediate layer portion 110 and a second intermediate layer portion 111. It should be understood that two or more dividing layers 109 may be used to subdivide the intermediate layer 103 into several intermediate layer portions. The diving layers 109 provide additional strength and support for the intermediate layer 103, especially when water or other liquid has been added to the intermediate layer 103 and the water-soluble fibers 107 have been dissolved into solution. Use of several dividing layers 109 allows the intermediate layer portions 110 and 111, which include water-soluble fibers 107, to remain thin and flexible after drying.

The entire thickness of the intermediate layer is preferably in the range of about 100 to 5000 microns, and most preferably within the range of about 500 to 3000 microns. Each dividing layer 109 is preferably between 30 and 100 microns. If more than one dividing layer 109 is used, it is preferred that they be spaced apart from each by a distance ranging from 50 and 100 microns. Preferably an additional layer of hydrophilic fibers should be added to the intermediate layer 103 for every 200 microns of thickness of the intermediate layer 103. The dividing layers 109 should be porous in order to allow water to pass between the various layers. A preferred pore size between the hydrophilic fibers in the dividing layer 109 is approximately 500 nanometers to 5 microns.

In the preferred embodiment the water-soluble fibers 107 are made from micro-fiber polymers. Examples of suitable polymers include poly (ethylene oxide), and polyvinylpyrrolidone, polyvinyl alcohol, or any other water soluble or gelling material, such as alginate, that is suitable for forming fibers. Similarly, the water insoluble fibers 108 are preferably micro-fiber polymers that include polyvinyl acetate, poly (caprolactone), poly (D,L-lactic acid), poly (glycolic acid), and similar co-polymers of these acids. The weight ratio of water-soluble fibers 107 to water insoluble fibers 108 within the intermediate layer 103 preferably ranges from between 20:80 to 80:20, and most preferably about 70:30.

The fiber forming and deposition techniques to form the intermediate layer 103 may be electro spinning from a solution, gas blowing from a melt or any other known technology. A preferred technique for forming the fibers and depositing them in a layer is shown and described in U.S. patent application Ser. No. 10/431,888 filed May 7, 2003 and U.S. patent application Ser. No. 10/382,422 filed Mar. 5, 2003. The fibers used to form the intermediate layer 103 may be colored for matching a patient's skin, or for other reasons. Additives may be incorporated into the fibers to enhance the antibacterial or antiviral properties of the fibers.

The inner layer 104 has an exposed surface 112 opposite from the intermediate layer 103 that serves as a wound facing surface (see FIG. 5). The inner layer 104 is preferably made of non-woven fibers that are at least partially hydrophilic so that excess moisture, or exudates from the wound, can be absorbed into at least the intermediate layer 103. It is preferred to form the inner layer 104 with a varying density such that the inner layer 104 has relatively large pores at its exposed surface 112, and relatively smaller pores at its interface with the intermediate layer 103. By graduating the pore size from larger to smaller as the inner layer 104 approaches the intermediate layer 103, the exterior portion of the inner layer 104 with the larger pores acts as a filter for heavy components of wound exudate, and thereby prevents clogging of the internal portion of the inner layer 104. Preferably, the pore size may be in the range of about 20-50 microns at the exposed surface 112 and may be reduced down to about 1-5 microns near the intermediate layer 103. The preferred range of thickness for the inner layer is between 30 and 200 microns, and most preferably between about 50 and 100 microns.

Figure 6:
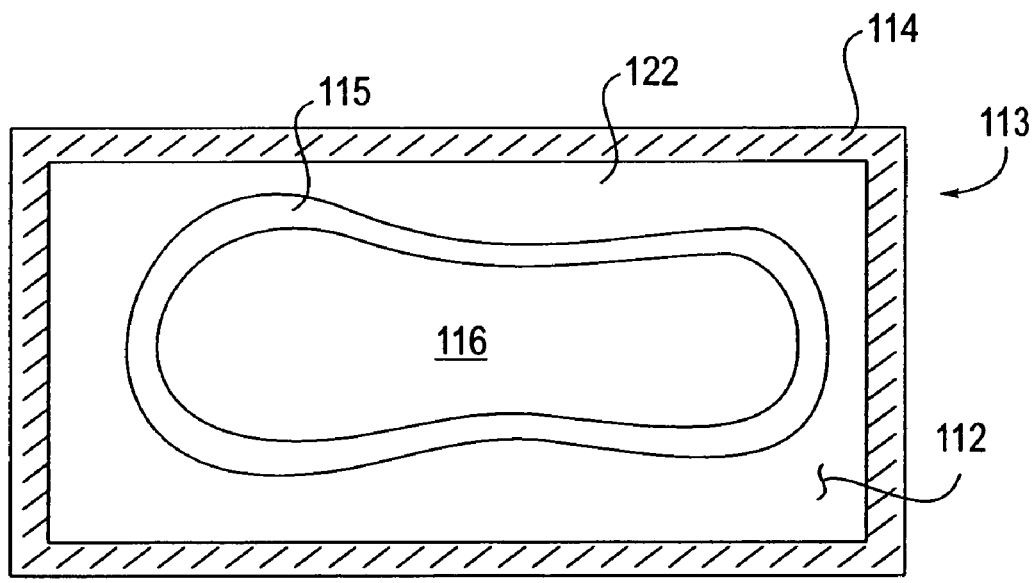
FIG. 6 is plan view of an embodiment of a wound dressing made from the piece of material of FIG. 1.

As discussed above, it is often desirable to maintain a portion of the wound moist, while permitting the skin directly surrounding the wound to remain dry. FIG. 6 shows a wound dressing 113 that is suitable for this purpose. A water repellent barrier 115 may be created that extends through at least the inner layer 104 and the intermediate layer 103. The portion of the wound dressing 113 circumscribed by the water repellent border 115 forms a moisture-retaining portion 116 of the wound dressing 113. A peripheral area 122 is typically provided outside the circumscribed moisture-retaining portion 116 for alignment with the skin surrounding the wound. On applying the wound dressing 113 to a user, the moisture-retaining portion 116 is preferably aligned with that portion of the wound that should be kept moist. The water repellent border 115 is preferably impermeable to water, saline solutions and glycerin. A mineral oil, or other similar oil-based product, or hydrophobic solution, gels or pastes are the preferred substances for forming the water repellent border 115, which may be formed by pouring or injecting the water repellent substance directly onto and through the exposed surface 112 of the inner layer 104. The width of the water repellent border 115 is preferably approximately equal to or slightly larger than the thickness of the wound dressing 113.

A skin-friendly medical adhesive 114 is applied to the peripheral area 122 of the exposed surface 112 for attachment of the wound dressing 113 to a user's skin in order to hold the wound dressing 113 in place. Those of skill in the art will be aware of numerous suitable adhesives. A preferred adhesive is sold under the tradename MASTISOL by Ferndall Laboratories, Inc. It is preferred that the adhesive 114 be applied to areas of the exposed surface 112 that will not be in direct contact with the wound. The density of adhesive 114 per area unit may be varied to create a lighter or stronger adhesion to the skin as desired. A person skilled in the art can easily determine the desired amount of adhesive for a particular application either by experience, or by a few simple experiments. It should also be understood that the adhesive 114 is not necessary. In this regard, the wound dressing 113 can be taped to the user's skin, or secured in place by wrappings such as gauze bandages.

Figure 7:
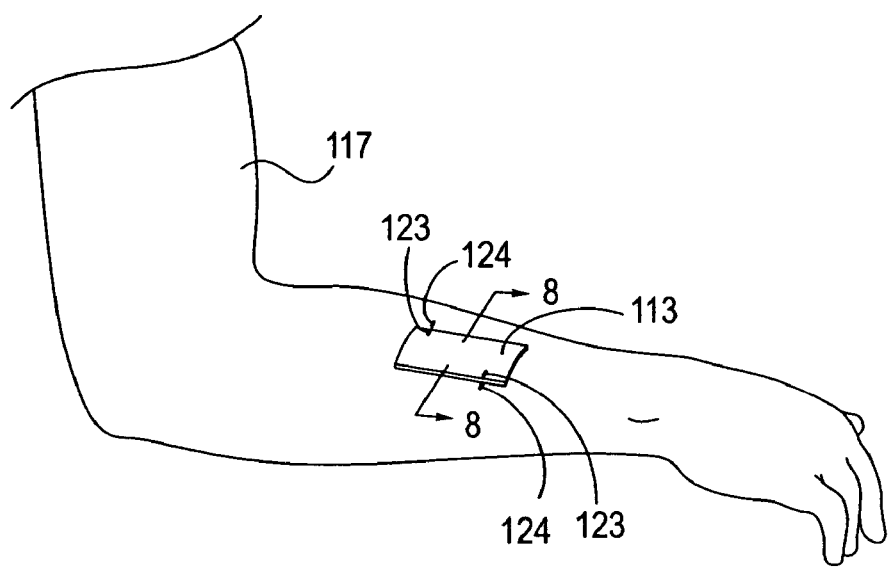
FIG. 7 is an isometric view of an arm with the wound dressing thereon.

A wound dressing 113 is shown attached to a human arm in FIG. 7. It should be understood that the wound dressing 113 has uses beyond wounds to the human body, and may be used to aid in the healing of other warm blooded animals, and especially other mammals. The dressing 113 is provided with one or more and preferably a pair of alignment markings 123 that are used to align the dressing 113 with one or more and preferably a pair of reference marks 124 that can be provided on the arm 117 as by felt tip pen or the like.

Figure 11:
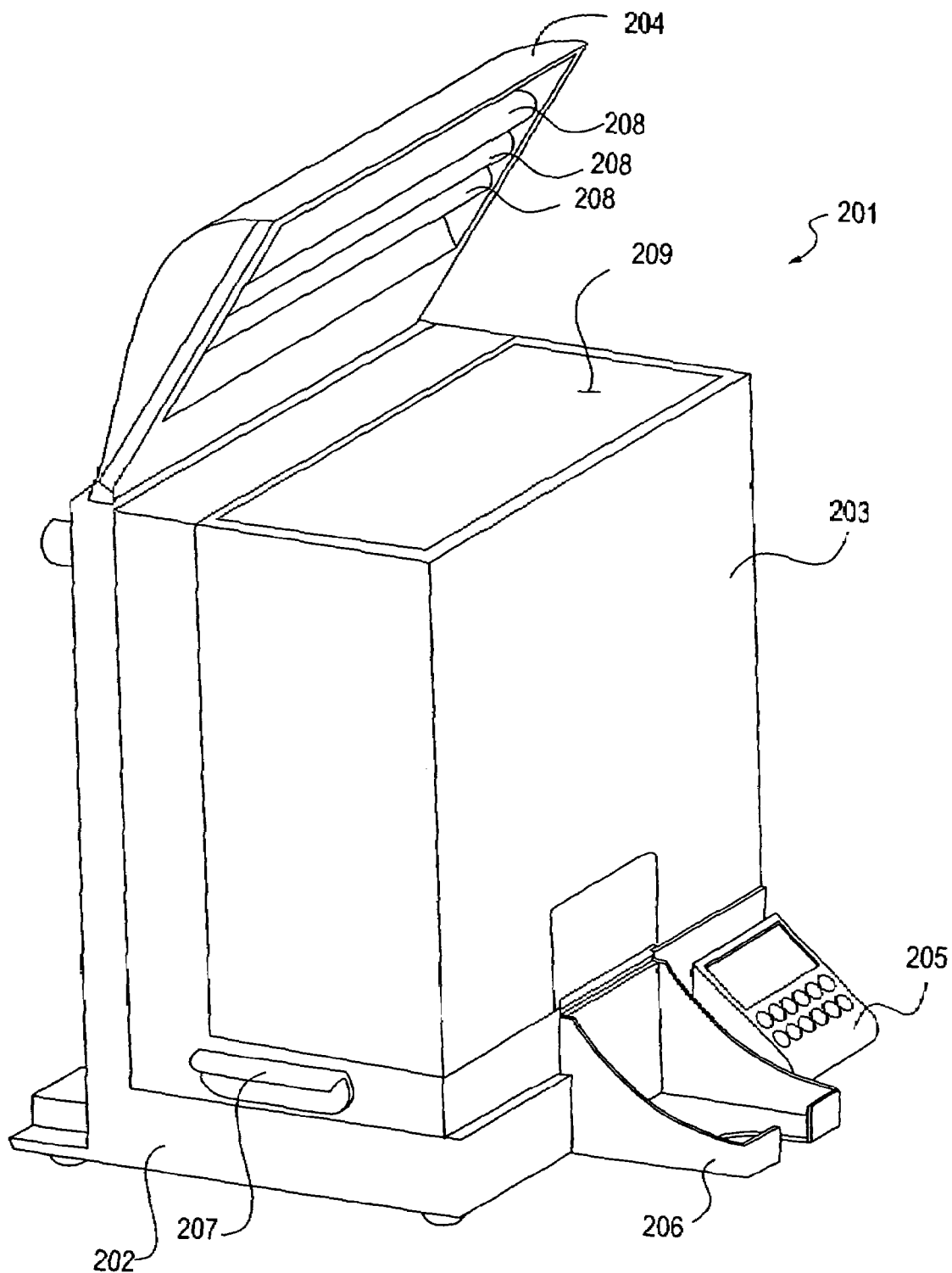
FIG. 11 is an isometric view of the apparatus of FIG. 10 with the top cover adjusted to an open position.
Figure 12:
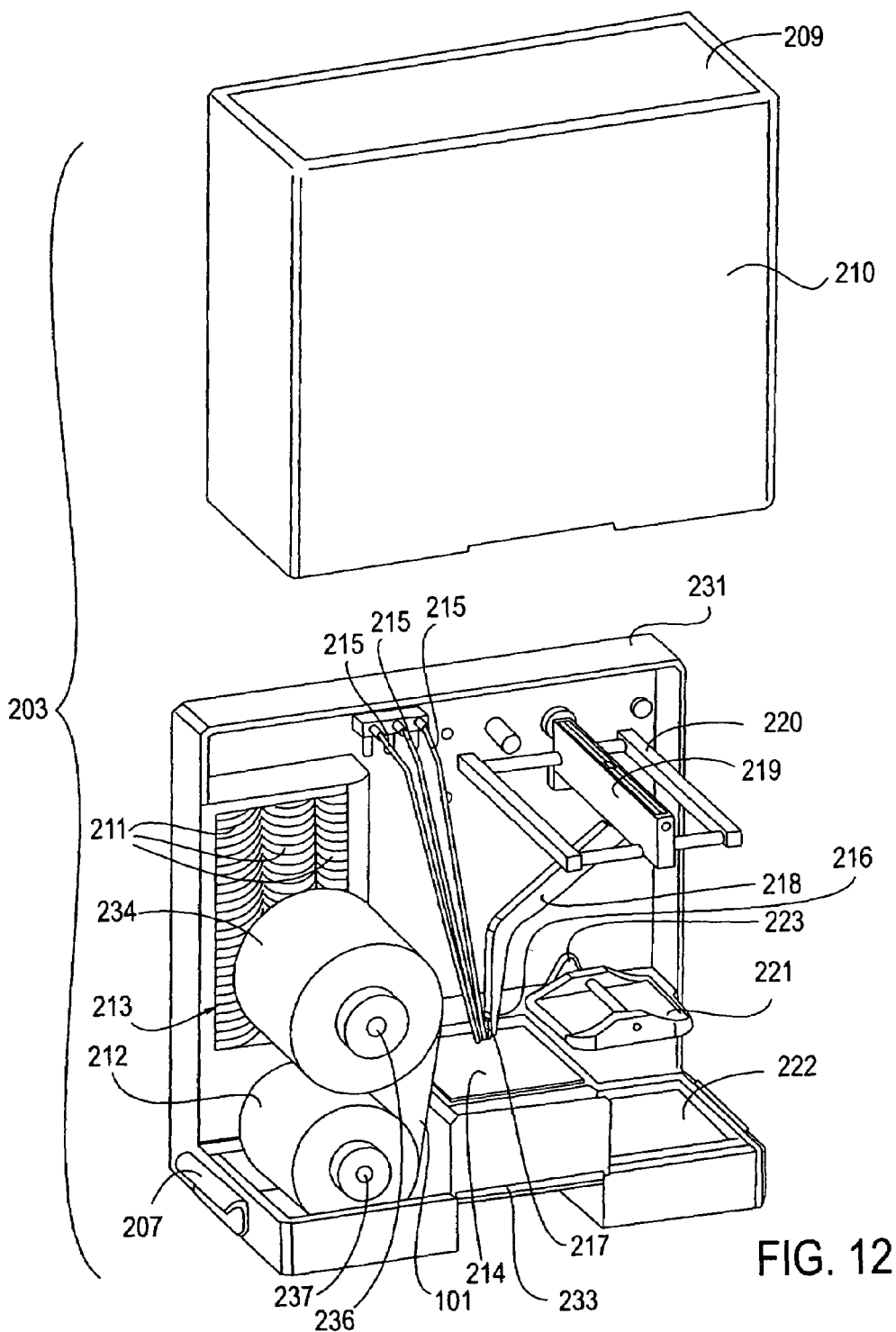
FIG. 12 is an isometric and exploded view of the detachable case portion of the apparatus of FIG. 10 illustrating the base portion with the cover portion removed to expose the interior portion of the detachable case portion.

An apparatus 201 that can be used to manufacture the dressing 113 is illustrated in FIGS. 10-15. The apparatus includes a base portion or base 202 and a case 203 that is detachable or removable from the base 202. The base 202 includes a controller and other electronic components for controlling the operation of the apparatus or machine 201. The base 202 includes electronic controls and display 205 that can be used to input information and commands and display the same or outputted information. The base 202 is connectable with a power supply through a power cord (not shown). Alternatively and additionally, it can be battery powered. A hinged lid 204 is attached to the base portion 202 and generally covers and sets on top of the removable case 203. A pair of handles 207 are provided along the sides of the removable case 203 to aid in carrying the case 203 and the machine 201. A receiving receptacle 206 is provided in the lower front center of the base portion 202 to receive the wound dressings 113 or package containing the would dressing manufactured by the machine 201. An output slot 233 is included for permitting ejection of the package or dressing from the machine, and can be formed at the juncture of the base 202 and the case 203. FIG. 11 shows the apparatus of FIG. 201 with the hinged lid 204 adjusted to an upward open position. In this orientation it can be seen that ultraviolet lights 208 are provided within the hinged lid 204. A window 209 is provided in the top of the removable case 203 to align with the ultra violet lights 208 when the hinged lid 204 is closed. The ultraviolet lights 208 can have a germicidal effect and can help to maintain a sterile environment inside the removable case 203. According to one embodiment the ultraviolet lights are germicidal low-pressure mercury-arc lamps available from Specialty Optical Systems, Inc.

The base 202 supports a removable frame 231 on which various components of machine 201 are mounted. Detachable case 203 includes the frame 231 and a cover 210 that can be removed from the frame 231 to expose the inner workings of the case 203. A gasket or seal (not shown) may be provided along the interface between the frame 231 and the cover 210 to create an airtight environment within the case 203 when the cover 210 is attached to the frame 231.

The material 101 used to make cut-out the dressings 113 is provided as a continuous strip. In a preferred embodiment the strip of material 101 is about one (1) mm thick, one hundred-fifty (150) mm wide, and ten (10) meters long. The supply of new material 101 is provided on a delivery roller 234, and the leftover material 101 that remains after the dressing 113 is cut out gets transferred on to an intake roller 212. The rollers 234 and 212 are mounted on delivery spindle 236 and intake spindle 237, respectively. In the preferred embodiment, the intake spindle 237 is driven, and the delivery spindle 236 is passive. The delivery spindle 236 is mounted on a pivoting spindle arm 238 (partially visible in FIG. 13) that is movable to move the delivery roller 234 from its rest position shown in FIG. 12 to the stretched-across-stage delivery position shown in FIG. 13. The intake spindle 237 is preferably stationary.

Figure 13:
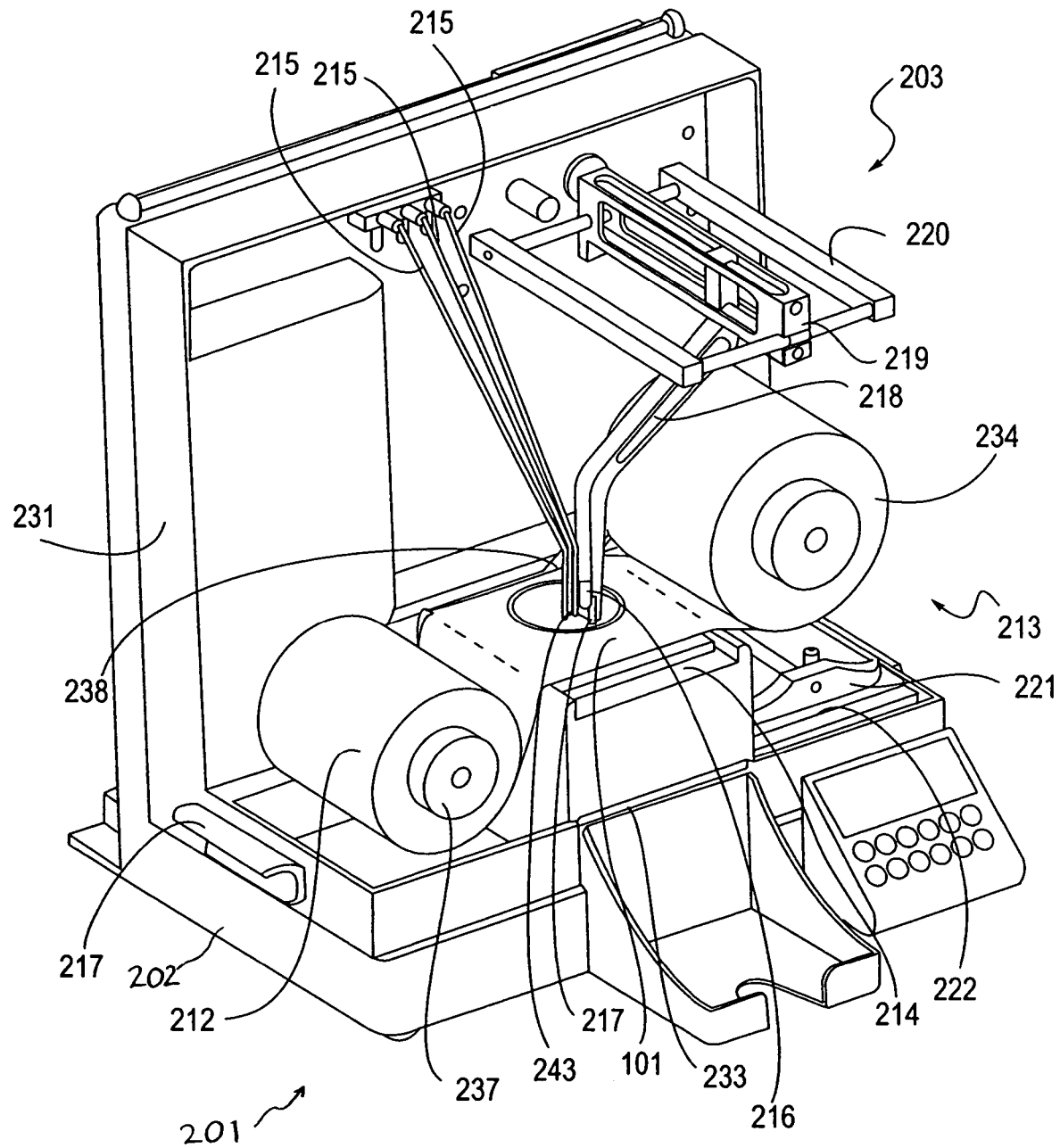
FIG. 13 is an isometric view of the detachable case portion of FIG. 12 with the top cover removed, the fabric dispenser adjusted to a dispensing position and the cutting head cutting the fabric to a desired shape.
Figure 14:
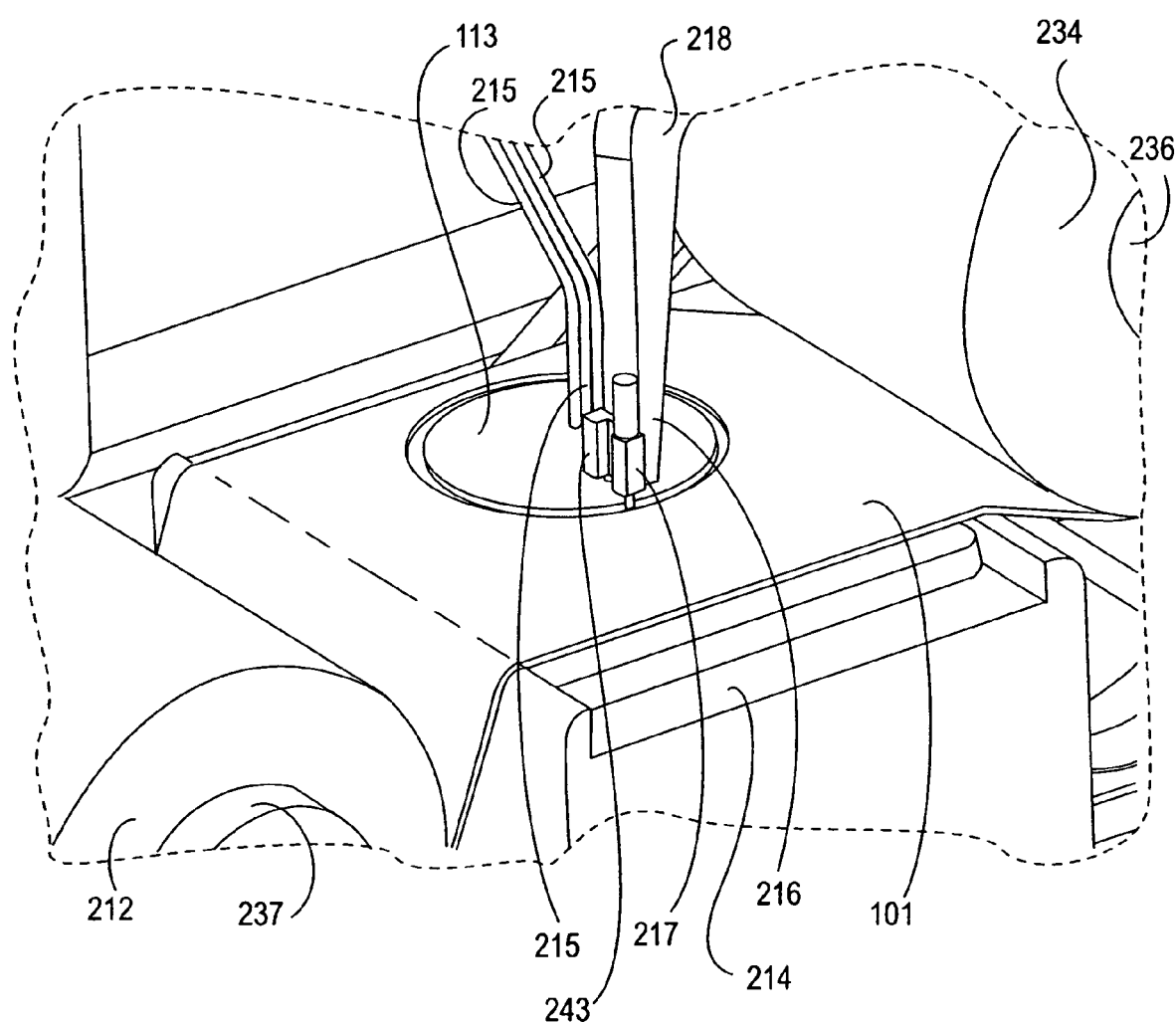
FIG. 14 is an enlarged isometric view of the fabric and cutting head of FIG. 13.

An upwardly facing stage 214 (including upwardly extending side projections and a recessed surface below them) is provided near the bottom center of the frame 231. When the delivery spindle 236 is adjusted to its delivery position of FIG. 13, the material 101 between the rollers 234 and 212 is stretched across the projections of stage 214 so that it may be worked upon by implements provided on a working head 216. The implements attached to the working head 216 include a cutting tool 217. It is appreciated that other suitable assemblies and mechanisms can be provided for delivering a stretched strip of material 101 to stage 214 for the formation of cut out dressing 113 as shown in FIGS. 13-14.

Reservoirs 211 are provided at the rear of the frame 231 and thus the rear of the case 203. These reservoirs 211 may hold the moisturizing substance, the adhesive, the water repellent substance used to form the water repellent barrier 115, and any other material used during the formation of the dressing 113. The reservoirs 211 are individually removable so that they can be replaced. Capillary tubes 215 connect to the reservoirs 211 (connection not shown) and connect with the nozzle 243 on the working head 216. Alternatively, each capillary tube 215 may have its own nozzle. Suitable actuators 240 (see FIG. 16) are provided to selectively dispense the liquids from the reservoirs 211 through the capillary tubes 215.

The cutting tool 217 may be a sharpened blade, or more preferably a heated element with a 45-degree angled cone-shaped head that will quickly melt through the material 101 to thereby shape the cut-out dressing 113. An element that will heat to approximately 350 degrees Celsius is preferred. A connection arm 218 connects the working head 216 with a movable carriage 219 mounted to carriage frame 220. The connection arm 218 is adjustably slidable within the movable carriage 219 in order to adjust the position of the working head 216 with respect to the stage 214 along a first axis. Similarly, the movable carriage 219 is adjustable on the carriage frame 220 to adjust the position of the working head 216 with respect to the stage 214 along a second axis that is orthogonal to the first axis. By adjusting the position of the movable carriage 219 on the carriage frame 220 and by adjusting the position of the connection arm 218 within the movable carriage 219, the position of the working head 216 can be adjusted to any position in a plane above the stage 214.

Figure 15:
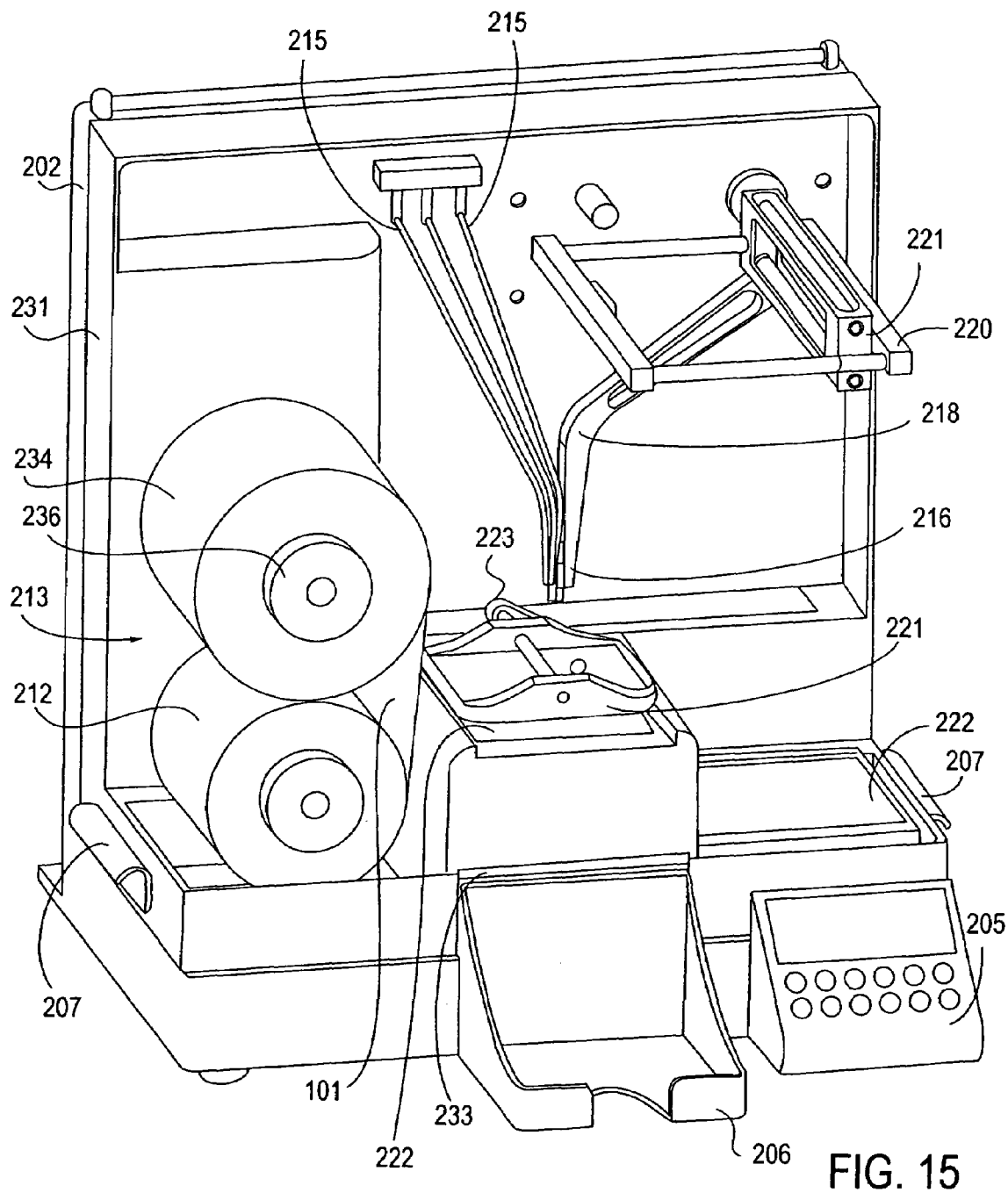
FIG. 15 is an isometric view of the apparatus of FIG. 10 with the top cover removed and the packaging tool adjusted to a packaging position.

A packaging tool 221 is movable to supply sheets of packaging paper 222 to the stage 214 in order to package the wound dressing 113 in a sterile package 226. (See FIGS. 18-19). The packaging tool 221 is mounted on a packaging tool arm 223 that is rotatable between a rest position that places the packaging tool 221 at a supply of packaging paper 222, as shown in FIG. 13 and a dispensing position that places the packaging tool near the stage 214 as shown in FIG. 15. (wherein one packaging sheet 222 is shown dropped onto the recessed surface of stage 214). A suitable motor and linkage (shown partially in FIG. 16) can be used to move the packaging tool arm 223. It is appreciated that other suitable assemblies and mechanisms can be provided for providing packaging paper 222 to stage 214 or otherwise packaging the completed dressing 113.

Figure 16:
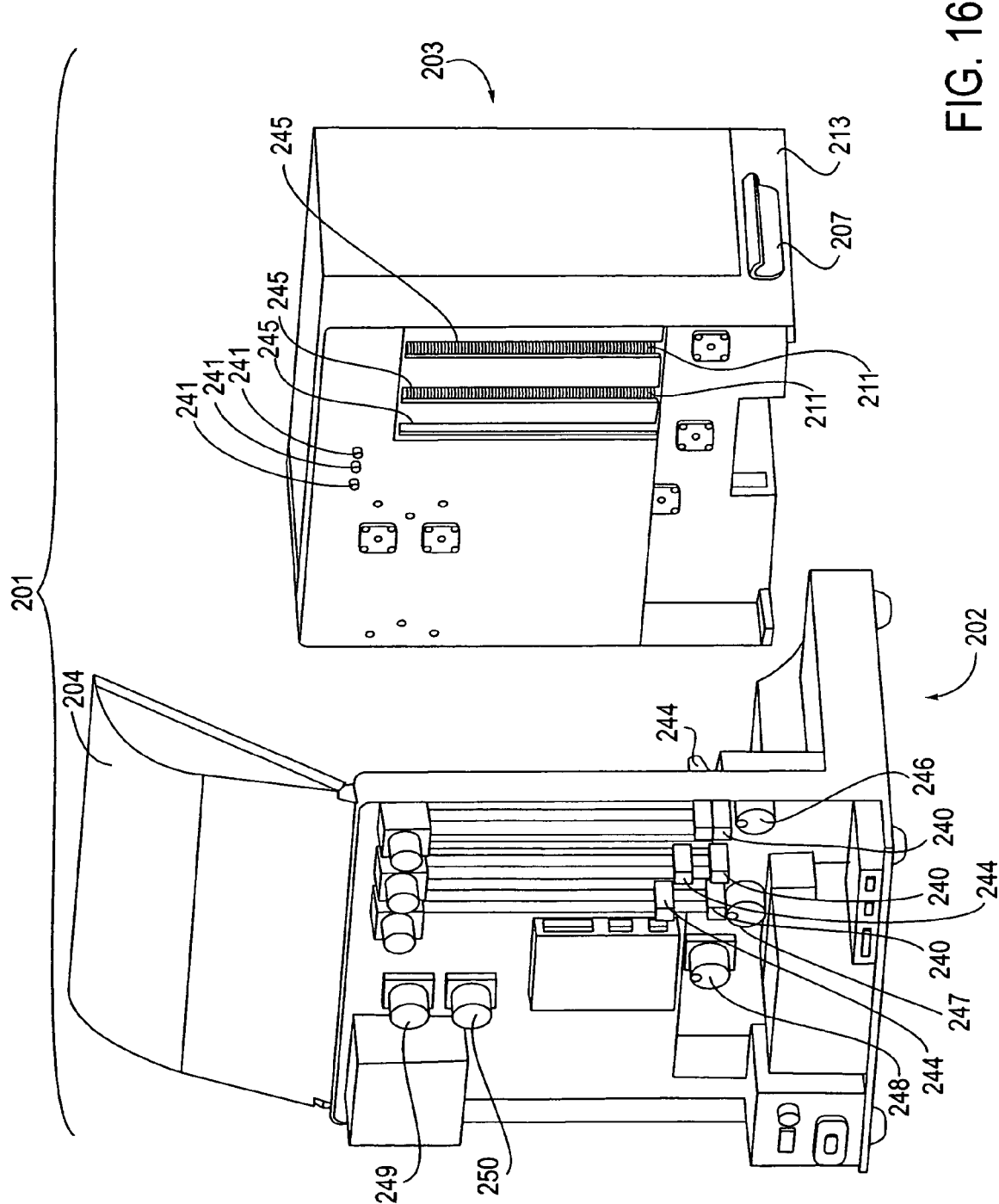
FIG. 16 is a rear isometric partially exploded view of the apparatus of FIG. 11.

FIG. 16 shows the connection between the base 202 and the removable case 203. Actuators 240 are provided to dispense the liquids out of the reservoirs 211 through capillary connectors 241 that lead to the capillary tubes 215. In the preferred embodiment, the reservoirs 211 are bellow bottles that collapse in an accordion-like fashion. The actuators 240 are connected to pressing plates 244 that extend through the rear portion of the base 202 into the rear of the case 203 through slots 245. The actuators 240 can be extended to move the press plates 244 upwardly, which in turn would in turn move the bottom of the bellow bottle reservoirs 211 upwardly, thereby forcing liquid up and out through the capillary tubes 215. Alternative structures, such as pumps or plungers may be used to dispense the liquids from the reservoirs 211. An air pump (not shown) may be mounted on the base 203 and connected to the case 203 by a passage (not shown) in order to provide a continuously positive pressure within the case 203, to maintain a sterile environment within the case 203.

With further reference to FIG. 16, an intake motor 246 mounted on the rear of the base 202 is attached to a shaft (not shown) that extends into the case 203 to rotate the intake spindle 237. A delivery motor 247 is mounted on the rear of the base 202, and engages a shaft (not shown) that extends into the case 203 to rotate the spindle arm 238. A packaging tool arm motor 248 is also mounted to the rear of the base 202, and drives a shaft (not shown) that extends into the case 203 to rotate the packaging tool arm 223. The intake motor 246, the delivery motor 247, and the packaging tool arm motor 248 may be gear motors available from the Nidec Copal Corporation under the HG16 series.

FIG. 16 also shows an X-axis motor 249 mounted to the back of the base 202 for adjusting connection arm 218 in and out relative to the rear of the frame 213 within the carriage 219. A Y-axis motor 250 is similarly mounted to the back of the base 202 for adjusting the connection arm 218 tranversely (left and right as viewed from the front) by moving the carriage 219 back and forth on the frame 220. In one embodiment, the X-axis motor and the Y-axis motor are 2-phase stepping motors from Oriental Motor, Inc. under the CSK series.

Figure 17:
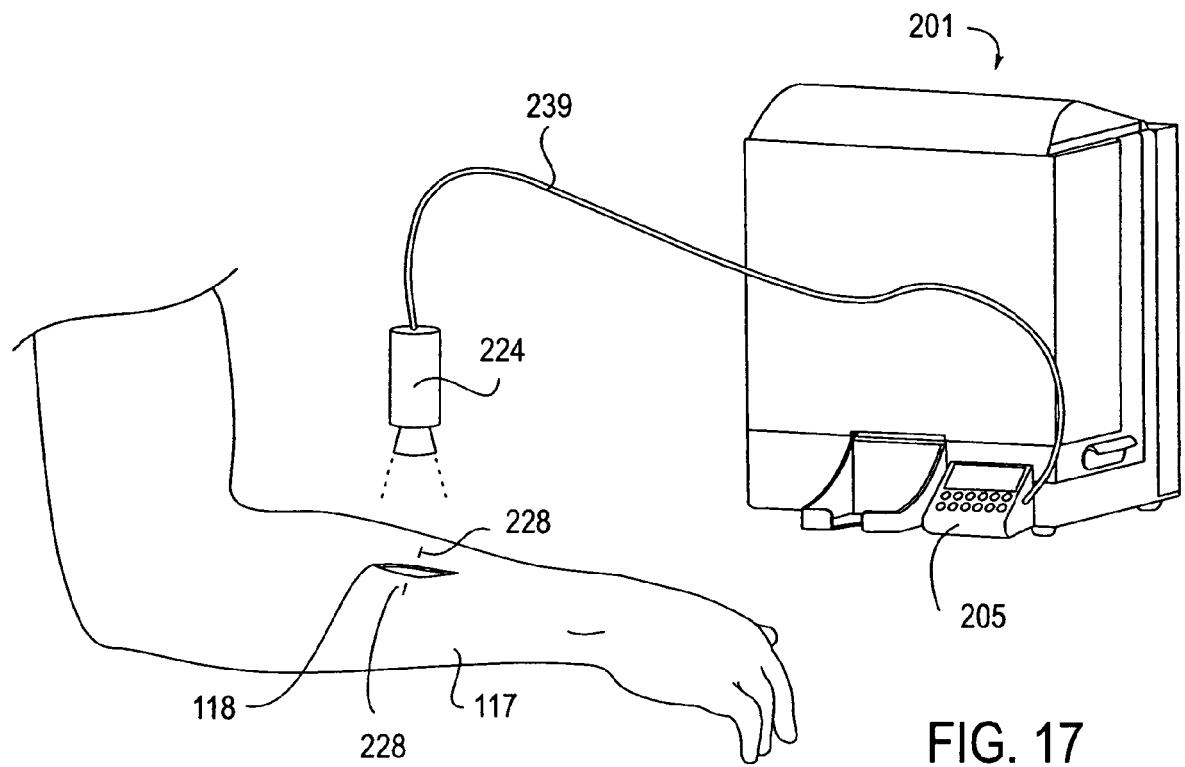
FIG. 17 is an isometric view of an arm with an undressed wound and the apparatus of FIG. 10 being used with an image capturing device to obtain an image of the wound.

FIG. 17 discloses an additional embodiment of the apparatus 201 that can be used to prepare a wound dressing 113. According to this embodiment, an image collection device 224, such as a digital camera, is used to collect an image of the wound 118. The image relating to the wound is downloaded to the electronic controls 205 of the apparatus 201, either by the use of cable 239 as shown, by a removable storage device or any other suitable means. The coordinates of various portions of the wound 118 are extracted from the image collection device.

Figure 18:
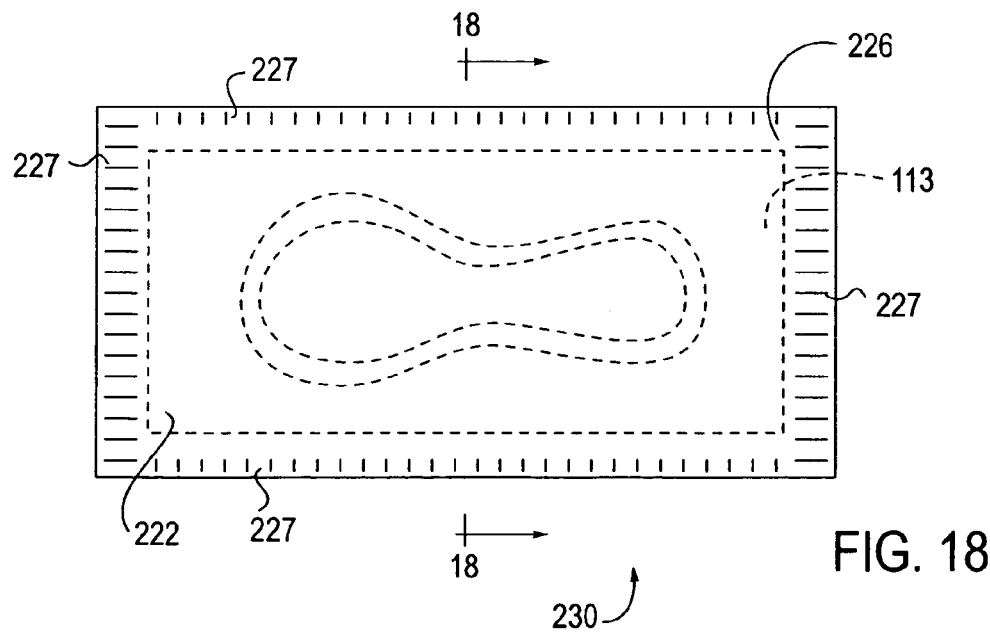
FIG. 18 is a top view of a package containing a dressing made by the apparatus of FIG. 10.
Figure 19:
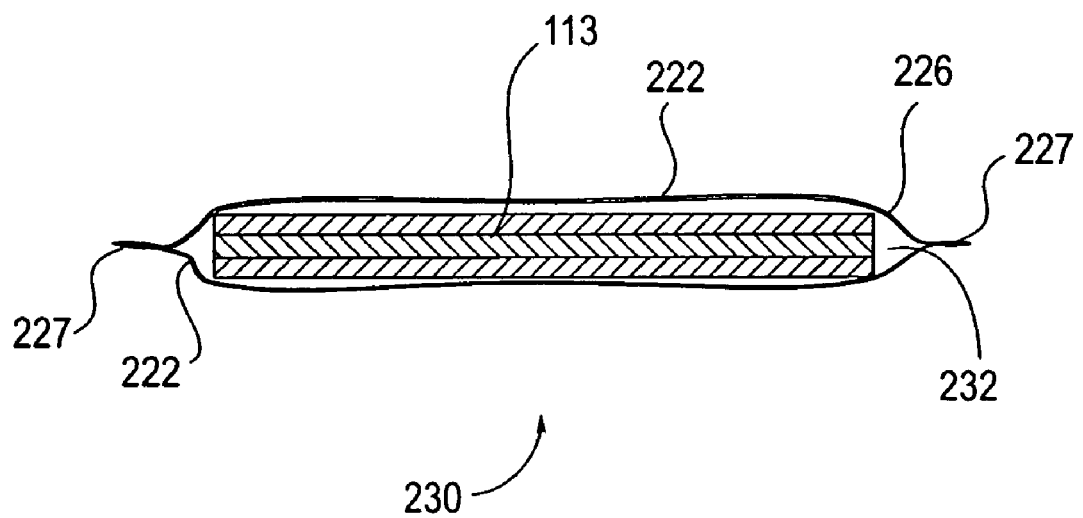
FIG. 19 is a cross-sectional view of the package of FIG. 17 taken along the line 19-19 of FIG. 18.

FIGS. 18 and 19 show a packaged dressing 230 made using the apparatus 201. Adhesive at the edges 227 of the packaging paper 222 holds the package 226 in the sealed condition to create a sterile chamber 232. The dressing 113 is contained within the sterile chamber 232.

Figure 8:
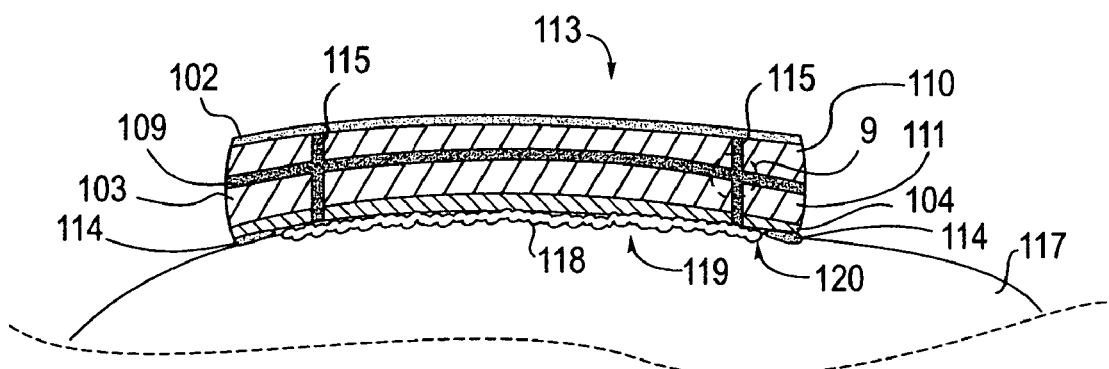
FIG. 8 is a partial cross-sectional view of the wound dressing and arm of FIG. 7 taken along line 8-8 of FIG. 7.

In use, as seen in FIG. 8, the wound dressing 113 is placed on the arm 117 and covers a wound 118. The wound 118 includes an exudating portion 119 located generally towards the interior of the wound, and a non-exudating portion 120 located generally at the periphery of the wound 118. The moisture-retaining portion 116 is aligned over the exudating portion 119 of the wound 118. The adhesive 114 holds the wound dressing 113 in place by adhering to the dry skin of the user's arm 117 outside the periphery of the wound.

Figure 9:
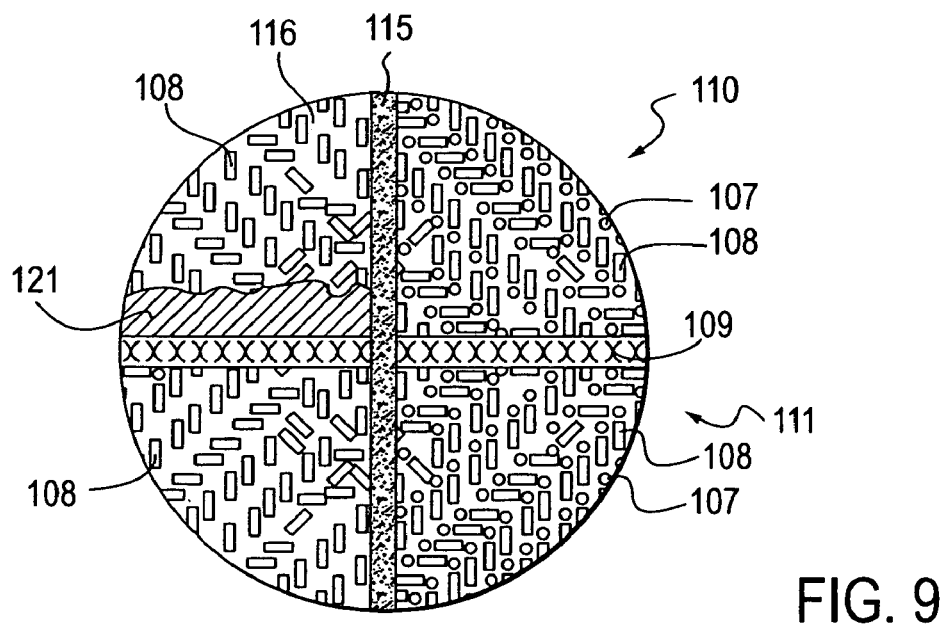
FIG. 9 is an enlarged view of a portion of FIG. 8 identified by the circle labeled 9 in FIG. 8.
Figure 10:
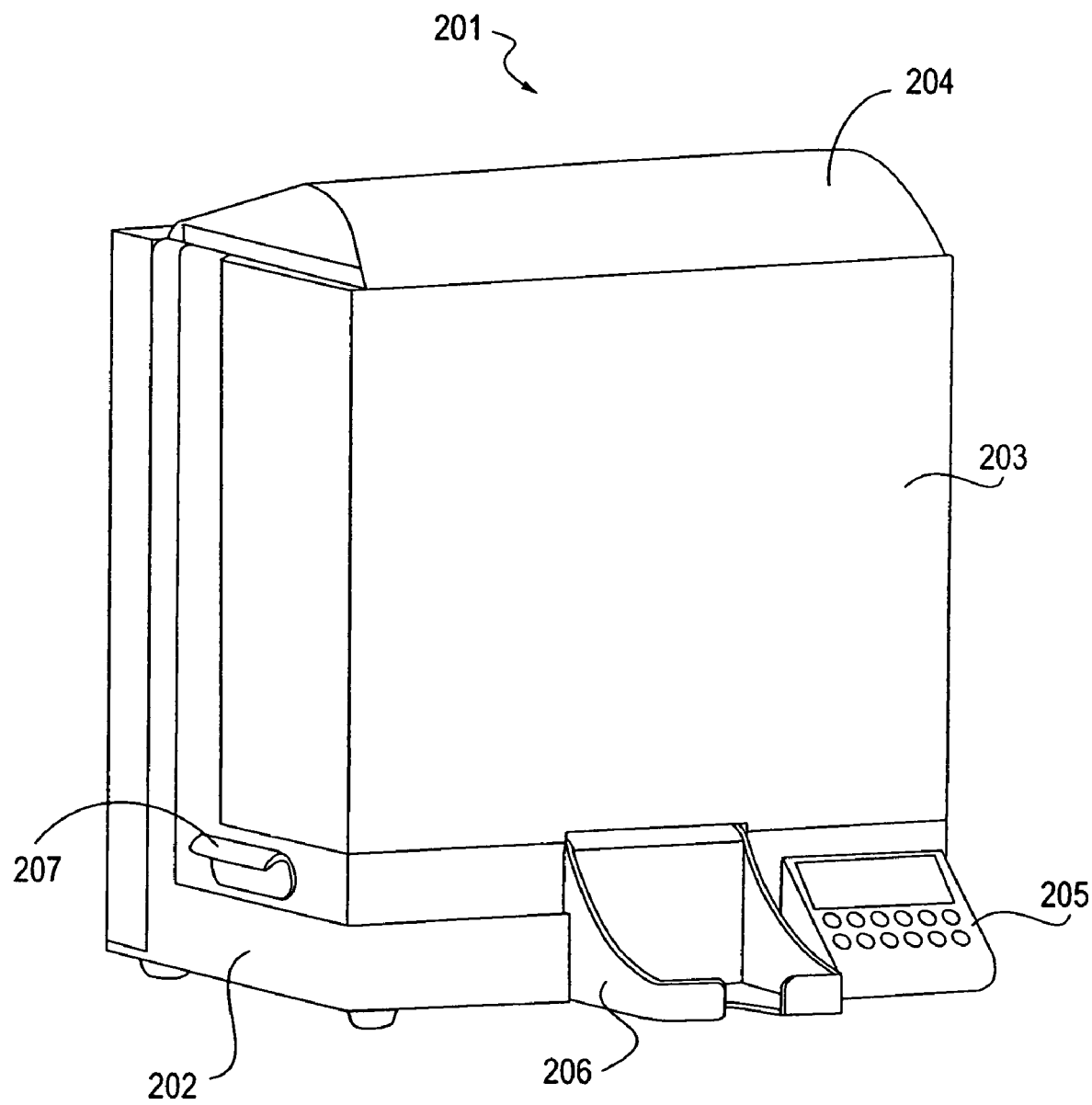
FIG. 10 is an isometric view of an embodiment of an apparatus of the present invention for manufacturing the wound dressing of FIG. 6.

As the exudating portion 119 of the wound 118 gives off liquid, that liquid is absorbed into the hydrophilic fibers of the inner layer 104, and may pass into the intermediate layer 103. In this fashion, excess drainage may be pulled away from the wound 118 by the wound dressing 113. As the liquid is drawn into the intermediate layer 103, it dissolves the water-soluble fibers 107 to form a solution of the liquid and soluble fibers that creates a film 121. FIG. 9 shows a detailed illustration of an intermediate layer 103 wherein liquid has been introduced into the intermediate layer 103 thereby dissolving the water-soluble fibers 107 and forming a viscous layer 121 that is the solution of the dissolved soluble fibers 107 and the liquid. The more wound liquid is absorbed from the wound the thicker the viscous layer 121. While the surface of the viscous layer 121, facing the outer layer 102, is wet, the water evaporates through the outer layer 102. The evaporation partially reduces accumulation of the wound liquids in the dressing and thickening the viscous layer 121. If the wound reduces intensity of exudate production then the evaporation from the viscous layer 121 results in forming a dry film on the surface of the viscous layer 121 facing the outer layer 102. The film serves as a moisture vapor barrier to keep the underlying layers of the dressing moist and prevent desiccation of the wound. The film 121 is impermeable to water vapor, and thereby precludes, or at least significantly reduces, any evaporation from layers of the dressing 113, or from the wound 118 located below the film 120.

Typically, rather than relying on the liquid exuded from the wound itself, it is desirable to pre-wet the moisture-retaining portion 116 of the dressing 113. Preferably a sterile water or water-based solution, such as saline or a mixture of water and glycerin is applied to the moisture-retaining portion 116 through the exposed surface 112 of the inner layer 104. Once the water soluble fibers 107 have been dissolved into solution, the moisture retaining portion 116 of cut-out the dressing 113 is converted from an absorbing function to a moisturizing function. Preferably this is done before application of the dressing 113 to the wound 118. The amount of moisturizing agent per area or volume unit of the moisture-retaining portion 116 may be varied to achieve a lighter or heavier moisturizing effect as desired. The structural integrity of the moisture-retaining portion 116 of the dressing 113 is maintained within the intermediate layer 103 by the water and soluble fibers 108, which are not deteriorated by the water, and by the hydrophilic fibers in the dividing layer 109.

Over time, and starting with the outermost viscous layer 121, the liquid will evaporate through the protective outer layer 102. As the water from each viscous layer 121 evaporates, the layer below it forms a film of dry polymer that serves as a moisture vapor transmission barrier that precludes, or at least retards evaporation, and the liquid therefore sequentially evaporates out of the dressing 113 more slowly than it otherwise would. Therefore, the dressing 113 automatically converts part of itself from absorbing to moisturizing, and moisturizing with self-protecting properties that slow down evaporation.

In operation, apparatus 201 is used to form a wound dressing 113, as shown in FIGS. 13-15. In FIG. 13 the material dispensing mechanism 213 has been adjusted to swing the intake delivery roller 212 up and over the stage 214 such that a portion of the material 101 is in a working position extending across the top of the prostrusions of stage 214. To achieve this, the connection arm 218 must be adjusted out of the way near the rear wall of the frame 231 to the position of FIG. 15. After the material 101 is stretched over the stage 214, the working head 216 can be moved back to a working position near to the material 101 to perform the various operations to form a cut-out wound dressing 113. and to thereafter selectively dispense any liquids if necessary thereon.

The operations to further form the cut-out wound dressing 113 include first forming the water repellant border 115 by moving the working head 216 in the desired shape to circumscribe the moisture-retaining portion 116 of the wound dressing 113. As the working head 216 moves in the desired shape, the water repelling substance is dispensed out of the corresponding capillary 215 onto the exposed surface 112 of the inner layer 104 of the material 101. When the speed the working head 216 and the rate of flow of the water repellant substance are properly calibrated, which for example can be accomplished through trial and error experimentation, a water repellant border of 115 of desired dimension is formed. The desired amount of moisturizing substance may then be added to the moisture-retaining portion 116 formed by the water repellant border 115 by again moving the working head 216 around the area circumscribed by the water repellant border and dispensing the moisturizing substance through the corresponding capillary tube 215. Adhesive may then be added in the desired configuration by moving the working head 216 through the correspondingly desired path and dispensing adhesive through the corresponding capillary tube 215. As mentioned above, the cutting tool 217 is used to cut the wound dressing 113 into the desired shape. FIG. 14 shows a close up detail of the cutting tool 217 cutting out material from strip 101 to thereby produce a wound dressing 113 having a circular shape. After completion of dispensing of selectively desired liquids if any onto cut-out dressing 113, the stage 214 can be tilted forward to permit the completed dressing 113 to slide off the stage 214 into the receptacle 206.

The packaging tool 221 is used to deliver sheets of packaging paper 222 to the stage 214 as shown in FIG. 15. Packaging tool arm 223 is used to adjust the packaging tool 221 back and forth between the supply of packaging paper 222 and the stage 214. If it is desired to package the dressing 113, a sheet of packaging paper 222 is positioned on the stage 214 prior to stretching the material 101 across the stage 214. Then, after the wound dressing 113 has been formed and cut from the sheet of material 101, the top roller 212 of the material dispensing mechanism 213 is adjusted back to the withdrawn position shown in FIG. 15 and a second sheet of paper is placed on top of the wound dressing 113 by the packaging tool 221. The heated cutting tool 217 can be used to apply heat to the peripheral edges of the packaging paper 222 in order to form a sealed chamber between the two sheets of packaging paper 222 and thereby provide a packaged dressing. Alternatively, a pressure sensitive adhesive may be provided as part of the packaging paper, in which case heat does not need to be applied, but the edges of the packaging paper 222 should be pressed together to activate the adhesive. The packaged dressing or package 230 can then be dispensed out of slot 233 to the receptacle by tilting the stage 214.

According to a further method of forming the dressing 113, the hot cutting tool 217 attached to the working head 216 can be used to selectively melt the edges of the dressing 113. This provides a more structurally sound dressing 113. Additionally, it tends to make the edges of the dressing 113 more dense, and hence thinner which is a desired feature.

The apparatus 201 of FIG. 17 can be used to make a dressing 113 according to an additional method. The information related to the coordinates of the wound 118, collected using the image collection device 224, are used to determine the size and shape of the dressing 113, as well as the size and shape of the moisture-retaining portion 116, as defined by the water repellant border 115. According to a preferred method of using the image collection device 224, one or more and preferably two reference marks 124 are made on the skin of the user surrounding the wound to serve as reference points. When the wound dressing 113 is prepared within the apparatus 201, one or more alignment markings 123 are made on the dressing 113, preferably by the hot cutting 217 tool, that correspond with or somehow relate to the coordinates of the reference marks 124 surrounding the wound 118. When the dressing 113 is applied to the wound 118, the alignment markings 123 on the dressing 113 are aligned with the reference marks 124 on the skin 228 in some manner to assure that the moisture-retaining portion 116 is properly aligned with the wound 117.

Therefore, an improved wound dressing 113 and apparatus 201 for making the dressing 113 has been described. By allowing a user to selectively keep appropriate portions of the wound moist, while also permitting absorption of excess exudates from the wound, the dressing 113 serves to provide a controllable moist environment for the would and aid in the healing process.

Although the present disclosure invention has provided detail descriptions with a certain degree of particularity, it is understood that the disclosure has been made by way of example only, and changes in detail or structure may be made without departing from the spirit of the invention as disclosed hererein.

What is claimed is:

1. An apparatus for forming a wound dressing for treating a wound on a mammalian body, the apparatus comprising:
    a movable frame,
    a stage provided on the frame,
    a first dispenser carried by the frame and structured for dispensing at least a portion of a sheet of dressing-forming material over the stage,
    a cutting tool,
    a tool movement mechanism carried by the frame, operatively coupled to the cutting tool and structured for providing selective movement of at least the cutting tool relative to the stage so that the cutting tool can selectively cut out from the dressing-forming material dispensed over the stage, a selectively shaped portion of the dressing-forming material so as to thereby define a wound dressing of a desired shape for treating a corresponding wound,
    a reservoir of moisturizing solution, and
    a second dispenser carried by the frame and structured to selectively apply the moisturizing solution to a targeted portion of the wound dressing to thereby selectively moisturize the targeted portion of the wound dressing.

2. The apparatus of claim 1, wherein the reservoir of moisturizing solution is coupled to the frame.

3. The apparatus of claim 1, further comprising:
    a reservoir of water-repellant substance; and
    a third dispenser carried by the frame and structured to selectively apply the water-repellant substance to a prespecified portion of the dressing-forming material so as to thereby define a correspondingly shaped water-repellant barrier at the prespecified portion of the dressing-forming material.

4. The apparatus of claim 3, wherein the corresponding shape of the water-repellant barrier includes a rounded section.

5. The apparatus of claim 1, wherein the wound dressing has a periphery, the apparatus further comprising:
    a reservoir of adhesive; and
    a fourth dispenser, carried by the frame and structured to selectively apply the adhesive on to at least a portion of the dressing-forming material defining the periphery of the wound dressing so as to thereby allow the periphery to adhere to the mammalian body.

6. The apparatus of claim 1, wherein said tool movement mechanism is structured to selectively move at least the cutting tool along two different axes of movement.

7. The apparatus of claim 6, further comprising:
    a second reservoir containing a water-repellant substance and a third reservoir containing an adhesive, said second and third reservoirs being carried by the frame,
    first, second and third capillaries respectively extending from the first recited reservoir and the second and third reservoirs to one or more dispensing nozzles for thereby dispensing the moisturizing solution, water repellant substance, and adhesive selectively to selectable portions of the dressing-forming material.

8. The apparatus of claim 1, further comprising:
    a third dispenser for dispensing first and second sheets of packaging material to be positioned respectively below and above the defined wound dressing;
    wherein the first and second sheets of packaging material can be hermetically sealed together to form a package containing the defined wound dressing.

9. The apparatus of claim 1, further comprising:
    a cover engageable with the frame for forming a chamber enclosing the first dispenser, the tool movement mechanism, the reservoir, and the second dispenser.

10. The apparatus of claim 9, wherein the cover includes a window that passes UV light from ultraviolet germicidal lamps.

11. The apparatus of claim 1, further comprising:
    a base;
    a detachable case that is detachably attachable to the base, the detachable case forming an enclosure enclosing and containing the first dispenser, the cuffing tool, the reservoir, and the second dispenser;
    wherein the detachable case has an outlet for dispensing the defined wound dressing of a desired shape out of the enclosure; and
    wherein the base provides support for the detachable case, and the base includes control electronics for controlling the first dispenser, the tool movement mechanism, and the second dispenser.

12. The apparatus of claim 11, wherein the case includes an ultraviolet light passing window and the base includes an ultraviolet germicidal lamp disposed for working alignment with the window for sustaining a sterile environment within said enclosure.

13. The apparatus of claim 11 further comprising an image acquiring apparatus for acquiring image data representing a wound disposed on a mammalian body and a mechanism for transmitting said data to said control electronics.

14. The apparatus of claim 1, wherein the desired shape includes a rounded section.

* * * * *